US005457119A

United States Patent [19]
Bonjouklian et al.

[11] Patent Number: 5,457,119
[45] Date of Patent: Oct. 10, 1995

[54] A89271 FACTORS AND PROCESSES FOR THEIR PRODUCTION

[75] Inventors: Roseanne Bonjouklian, Zionsville, Ind.; Richard E. Moore; Gregory M. L. Patterson, both of Honolulu, Hi.; Tim A. Smitka, Indianapolis, Ind.

[73] Assignee: Eli Lilly and Company, Indianapolis, Ind.

[21] Appl. No.: 273,079

[22] Filed: Jul. 8, 1994

Related U.S. Application Data

[62] Division of Ser. No. 135,931, Oct. 13, 1993, Pat. No. 5,366,890, which is a division of Ser. No. 946,501, Sep. 16, 1992, Pat. No. 5,292,650, which is a continuation-in-part of Ser. No. 784,299, Oct. 29, 1991, abandoned.

[51] Int. Cl.$^6$ .................... A61K 31/275; C07D 209/94; C07D 405/02
[52] U.S. Cl. .................... 514/410; 548/417; 548/419; 548/425
[58] Field of Search .................... 514/410; 548/417, 548/419, 425

[56] References Cited

U.S. PATENT DOCUMENTS

| | | | |
|---|---|---|---|
| 4,755,610 | 7/1988 | Moore et al. | 548/425 |
| 4,803,217 | 2/1989 | Schwartz et al. | 514/409 |
| 4,870,185 | 9/1989 | Bonjouklian et al. | 548/148 |

OTHER PUBLICATIONS

Bonjouklian, et al.; C.A.; 120:268346 (1994).
Bonjouklian, et al.; C.A.; 119:158354 (1993).
Smitka, et al.; C.A.; 116:79985 (1992).
Moore, et al.; J. Org. Chem. (1987), 52, pp. 3773–3777.
Bonjouklian, et al.; J. Org. Chem. (1988), 53, pp. 5866–5870.
Bornemann, et al.; J. Am. Chem. Soc. (1988), 110, pp. 2339–2340.
Smitka, et al., J. Org. Chem., 57: 857–861, (1992).
R. E. Schwartz et al., "Unusual Cyclopropane–Containing Hapalindolinones from a Cultured Cyanobacterium", *J. Org. Chem.* 52, 3704–3706 (1987).
R. E. Moore et al., "Hapalindoles: New Alkaloids from the Blue–Green Alga *Hapalosiphon fontinalis*", *J. Am. Chem. Soc.* 106, 6456–6457 (1984).
R. E. Moore et al., "Hapalindoles, Antibacterial and Antimycotic Alkaloids from the Cyanophyte *Hapalosiphon fontinalis*", *J. Org. Chem.* 52, 1036–1043 (1987).
F. Valeriote et al., "Discovery of Anticancer Agents from Natural Products in a New In Vitro Screen," Intern. Res. Congress on Natural Products, Chicago, IL., Jul. 21–26, (1991).
F. Valeriote et al., "Discovery of Anticancer Activities in Blue–Green Algae and Marine Organisms," Proc. Am. Assn. Cancer Res. 32, 402 (1991).

*Primary Examiner*—Joseph P. Brust
*Attorney, Agent, or Firm*—Steven A. Fontana

[57] ABSTRACT

New hapalindole-type alkaloids called A89271 A–F and I are antifungal and antitumor agents. Methods for preparing them and for preparing hapalindoles G and H by culturing the blue-green alga *Fischerella ambigua* ATCC 55210 are provided. Methods for preparing A89271 factors B and F by culturing the blue-green alga *Hapalosiphon hibernicus* ATCC 55225 and a biologically pure culture of this alga are also provided. Further provided are methods and compositions for the inhibition of fungal growth and the treatment of susceptible neoplasms.

14 Claims, No Drawings

A89271 FACTORS AND PROCESSES FOR THEIR PRODUCTION

This application is a division of prior application Ser. No. 08/135,931, filed Oct. 13, 1993, (now U.S. Pat. No. 5,366,890) which is a divisional of application Ser. No. 07/946,501, filed Sep. 16, 1992, (now U.S. Pat. No. 5,292,650), which is a continuation-in-part of application Ser. No. 07/784,299, filed Oct. 29, 1991, now abandoned.

SUMMARY OF THE INVENTION

This invention relates to new hapalindole-type alkaloids that were isolated from the blue-green alga *Fischerella ambigua* ATCC 55210. The new alkaloids, called A89271 factors A–F and I, are antifungal and antitumor agents. In another aspect, this invention relates to several processes. One is a process for producing A89271 B that comprises culturing a blue-green alga selected from *F. ambigua* ATCC 55210, *Hapalosiphon hibernicus* ATCC 55225 and *Westiellopsis prolifica* Janet (UH isolate EN-3-1), or a mutant thereof that produces A89271 B. Another is a process for producing A89271 F that comprises culturing a blue-green alga selected from *F. ambigua* ATCC 55210 and *H. hibernicus* ATCC 55225 or a mutant thereof that produces A89271 F. Still another is a process for preparing an A89271 factor selected from A89271 factors A, C, D, E and I that comprises culturing *F. ambigua* ATCC 55210 or a mutant thereof that produces the selected A89271 factor. Yet another is a process for preparing a hapalindole selected from hapalindoles G and H that comprises culturing *F. ambigua* ATCC 55210 or a hapalindole G or H-producing mutant thereof. This invention also relates to a biologically purified culture of *Hapalosiphon hibernicus* ATCC 55225 or an A89271-producing mutant thereof. Furthermore, this invention relates to methods of using A89271 factors for inhibiting fungal growth, and for treating susceptible neoplasms in mammals. This invention also provides pharmaceutical compositions of one or more A89271 factors.

DETAILED DESCRIPTION

This invention relates to new antifungal and antitumor agents. In particular, this invention provides useful new hapalindole-type alkaloids called A89271 factors A, B, C, D, E, F and I. Other hapalindole-type alkaloids have been described by Bonjouklian et al. in U.S. Pat. No. 4,870,185 (issued Sep. 26, 1989) and by Moore et al. in U.S. Pat. No. 4,755,610 (issued Jul. 5, 1988).

Hapalindoles are potent fungicides that were first found in *Hapalosiphon fontinalis* R. E. Moore et al., *J. Am. Chem. Soc.* 1984, 106, 6456–6457; R. E. Moore et al., *J. Org. Chem.* 1987, 52, 1036; and R. E. Schwartz et al., *J. Ind. Microbiol.* 1990, 5, 113–124). The most common hapalindole, hapalindole A, is a chlorine- and isonitrile-containing, tetracyclic indole alkaloid that appears to be biosynthesized from precursors derived from tryptophan and geraniol pyrophosphate.

Similar compounds, the hapalindolinones, have been isolated from a Fischerella sp. (R. E. Schwartz et al., *J. Org. Chem.* 1987, 52, 3706–3708). Fischerella and Hapalosiphon both belong to the Stigonemataceae family (Stigonematales).

We have found a new series of hapalindole-related alkaloids, the A89271 factors. A89271 factors A–F are also called "ambiguines".

Like the hapalindoles, the A89271 factors are also produced by blue-green algae species belonging to the family Stigonemataceae, viz. *Fischerella ambigua* (Nageli) Gomont (UTEX 1903) ATCC 55210, *Hapalosiphon hibernicus* W. & G. S. West (UH isolate BZ-3-1) ATCC 55225 and *Westiellopsis prolifica* Janet (UH isolate EN-3-1). *F. ambigua* ATCC 55210 (UTEX 1903) was publically available and purchased from the Culture Collection of Algae Department of Botany, The University of Texas at Austin, Austin, Tex. 78713-7640. The A89271 factors of this invention can best be prepared by culturing the blue-green alga *Fischerella ambigua* ATCC 55210.

The A89271 factors have the following structures and numbering system:

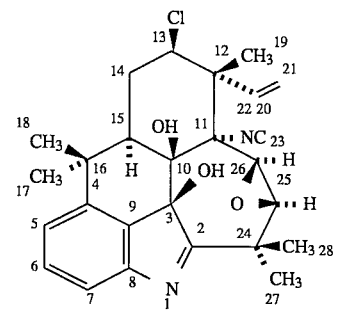

(1) A89271 A

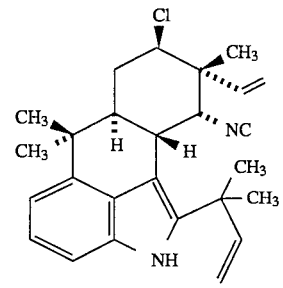

(2) A89271 B

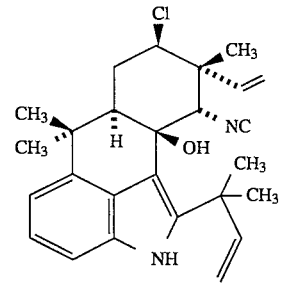

(3) A89271 C

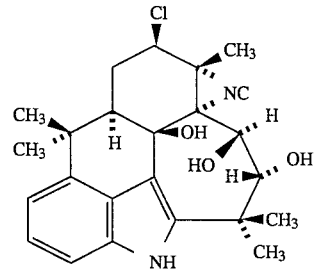

(4) A89271 D

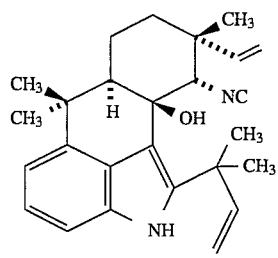

(5) A89271 E

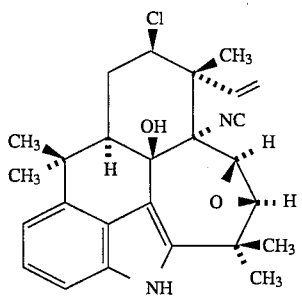

(6) A89271 F

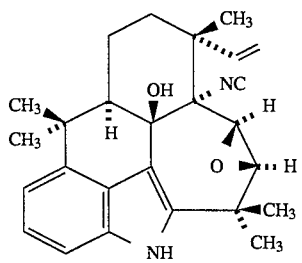

(7) A89271 I

The A89271 factors of this invention can be produced by cultivating an A89271-producing strain of the blue-green alga *Fischerella ambigua*. A89271 B can also be produced by cultivating an A89271 B-producing strain of *Hapalosiphon hibernicus* and *Westiellopsis prolifica;* and A89271 F can also be produced by *H. hibernicus*.

The A89271-producing *Fischerella ambigua* strain has been deposited in compliance with the Budapest Treaty and made part of the stock culture collection of THE AMERICAN TYPE CULTURE COLLECTION (ATCC), 12301 Parklawn Drive, Rockville, Md. 20852, from which it is available to the public under the Accession No. ATCC 55210.

The A89271-B-producing *Westiellopsis prolifica* strain is available from the culture collection of The University of Hawaii.

The New *Hapalosiphon hibernicus* W. et G. S. West

Strain: ATCC 55225

The novel strain of *Hapalosiphon hibernicus* of this invention produces A89271 factors B and F. This strain has been deposited in compliance with the Budapest Treaty, and made part of the stock culture collection of the ATCC, from which it has been assigned the accession number ATCC 55225. The permanency of this culture and the ATCC 55210 culture at the ATCC, Rockville, Md., and ready accessibility thereto by the public, are afforded throughout the effective life of the patent in the event the patent is granted. Access to each culture is available during pendency of the application under 37 C.F.R. §1.14 and 35 U.S.C. §112. All restrictions on the availability to the public of the cultures will be irrevocably removed upon granting of the patent.

Characteristics of *H. hibernicus* ATCC 55225:

Thallus is a true-branched filament. Cells of the main filament are 8 to 10 micrometers broad. The cells are quadrate to subcylindrical. Portions of the main filament are pleuriseriate. Heterocysts in the main filament are 5 to micrometers broad by 10 to 12 micrometers long (cylindrical). Filaments are richly branched. The cells of the branches are 4 to 6 micrometers broad and are thinner than those of the main filament. Cells near the tips of branches become substantially longer than broad (approximately 3 to 4 times as long as broad). The sheath is thin and hyaline (colorless).

As is the case with other organisms, the characteristics of the *Fischerella ambigua* ATCC 55210, *Hapalosiphon hibernicus* ATCC 55225 and the *Westiellopsis prolifica* strains that produce the ambiguines are subject to variation. Thus, natural and induced mutants of these strains may be obtained by recognized procedures, such as treatment with the chemical mutagen N-methyl-N'-nitro-N-nitrosoguanidine. Mutants of the *F. ambigua* ATCC 55210, *H. hibernicus* ATCC 55225 and *W. prolifica* cultures that retain the characteristic of producing an A89271 factor selected from A–F and I are contemplated by this invention.

The A89271 alkaloids of this invention can be prepared by culturing the *Fischerella ambigua, Hapalosiphon hibernicus* or *Westiellopsis prolifica* strain under submerged aerobic conditions in a suitable culture medium until substantial antifungal activity is produced. Other culture techniques, such as surface growth on solidified media, can also be used to produce these compounds.

The medium used to grow *Fischerella ambigua* ATCC 55210, *Hapalosiphon hibernicus* ATCC 55225 or the *Westiellopsis prolifica* culture can be any one of a number of media. Economy in production, optimal yield, and ease of product isolation are factors to consider when choosing the carbon and nitrogen sources to be used. Among the nutrient inorganic salts which can be incorporated in the culture medium are the customary soluble salts capable of yielding iron, potassium, sodium, magnesium, calcium, ammonium, chloride, carbonate, phosphate, sulfate, nitrate and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 mL/L) of an antifoam agent such as polypropylene glycol (M. W. about 2,000) to large-scale fermentation medium, if foaming becomes a problem.

For production of substantial quantities of the A8927! factors, submerged aerobic cultivation in tanks can be used. Small quantities may be obtained by shake-flask culture. Because of the time lag in production commonly associated with inoculation of large tanks with the organism, it is preferable to use a vegetative inoculum. The vegetative inoculum is prepared by inoculating a small volume of culture medium with the spore or akinete-containing form or fragments of the vegetative trichome of the organism to obtain a fresh, actively growing culture of the organism. The vegetative inoculum is then transferred to a larger tank. The medium used for the vegetative inoculum can be the same as that used for larger fermentations, but other media can also be used.

*Fischerella ambigua* ATCC 55210, *Hapalosiphon hibernicus* ATCC 55225 and *Westiellopsis prolifica* can be grown at temperatures between about 20° and about 30° C. The A89271 compounds are produced at a temperature of about 24° C. and an incident illumination intensity of 150–200 µEinsteins $m^{-2}$ $sec^{-1}$. Light intensity somewhat higher or lower can be used to produce the compounds.

As is customary in aerobic submerged culture processes of this type, $CO_2$ in sterile air is bubbled through the culture medium. For efficient production of the A89271 compounds, the percent of $CO_2$ should be about 1% (at 24° C. and one atmosphere of pressure).

A89271 production can be followed during the cultivation by testing samples of the mycelial extract via high-performance liquid chromatography or thin layer chromatography assays. Otherwise, samples of the mycelial extract can be tested against organisms known to be sensitive to these antifungal agents. One useful assay organism is *Candida albicans*.

Following their production under submerged aerobic cultivation conditions, the A89271 factors can be recovered from the cultivation medium by methods used in this art. Recovery is generally accomplished by initially filtering the culture medium to separate the algal cells and then freeze-drying the separated cells. The freeze-dried alga can be extracted with a suitable solvent such as isopropanol, dichloromethane, ethyl acetate or mixtures thereof. The alkaloids can be separated by subjecting this extract to separation techniques understood in the art, e.g. gel filtration and/or silica-gel chromatography. The alkaloids can be purified by high-performance liquid chromatography (HPLC).

The A89271 factors of this invention inhibit the growth of various fungi, particularly pathogenic animal and plant fungi.

Tables 1–7 summarize the minimum inhibitory concentrations (MIC's) at which the factors typically inhibit various fungi. In those tables, a dash or "N.T." means the material was not tested.

TABLE 1

In Vitro Antifungal Activity of A89271 A
in RPMI and 10% Fetal Calf Serum Broth

| | MIC (mcg/mL) | |
| --- | --- | --- |
| Compound | Candida albicans | Trichophyton mentagrophytes |
| A89271 A | 2.5 | >20 |
| Amphotericin B | 0.156 | — |
| Tolnaftate | — | 0.039 |

TABLE 2

In Vitro Antifungal Activity of A89271 A
in Sabouraud's and Dextrose Broth

| | MIC (mcg/mL) | | |
| --- | --- | --- | --- |
| Compound | Candida albicans | Trichophyton mentagrophytes | Aspergillus fumigatus |
| A89271 A | 2.5 | 10 | 80 |

TABLE 2-continued

In Vitro Antifungal Activity of A89271 A
in Sabouraud's and Dextrose Broth

| | MIC (mcg/mL) | | |
| --- | --- | --- | --- |
| Compound | Candida albicans | Trichophyton mentagrophytes | Aspergillus fumigatus |
| Amphotericin B | 0.625 | — | 1.25 |
| Tolnaftate | — | 0.039 | — |

TABLE 3

In Vitro Antifungal Activity of A89271 B,
C, D and F in RPMI & 10% Fetal Calf Serum Broth

| | MIC (mcg/mL) | |
| --- | --- | --- |
| Compound | Candida albicans | Trichophyton mentagrophytes |
| A89271 B | 1.25 | 2.5 |
| A89271 C | 1.25 | 0.625 |
| A89271 D | 1.25 | 0.625 |
| A89271 F | 1.25 | 1.25 |
| Amphotericin B | 0.156 | — |
| Tolnaftate | — | <0.02 |

TABLE 4

In Vitro Antifungal Activity of A89271 B,
C, D and F in Sabouraud's and Dextrose Broth

| | MIC (mcg/mL) | | |
| --- | --- | --- | --- |
| Compound | Candida albicans | Trichophyton mentagrophytes | Aspergillus fumigatus |
| A89271 B | 1.25 | >80 | 20 |
| A89271 C | 2.5 | >80 | >80 |
| A89271 D | 1.25 | >80 | >80 |
| A89271 F | 1.25 | >80 | >80 |
| Amphotericin B | 0.312 | — | 1.25 |
| Tolnaftate | — | <0.02 | — |

TABLE 5

In Vitro Antifungal Activity of A89271 E
and I in RPMI and 10% Fetal Calf Serum Broth

| | MIC (mcg/mL) | | |
| --- | --- | --- | --- |
| Compound | Candida albicans | Trichophyton mentagrophytes | Aspergillus fumigatus |
| A89271 E | 2.5 | 2.5 | >80 |
| A89271 I | 1.25 | 2.5 | >80 |
| Amphotericin B | 0.625 | N.T. | 1.25 |
| Tolnaftate | N.T. | 0.02 | N.T. |

TABLE 6

In vitro Antifungal Activity of A89271 E
and I in Sabouraud's and Dextrose Broth

| | MIC (mcg/mL) | | |
| --- | --- | --- | --- |
| Compound | Candida albicans | Trichophyton mentagrophytes | Aspergillus fumigatus |
| A89271 E | 5 | 2.5 | >80 |

TABLE 6-continued

In vitro Antifungal Activity of A89271 E
and I in Sabouraud's and Dextrose Broth

| Compound | MIC (mcg/mL) | | |
|---|---|---|---|
| | Candida albicans | Trichophyton mentagrophytes | Aspergillus fumigatus |
| A89271 I | 2.5 | 2.5 | >80 |
| Amphotericin B | 0.312 | N.T. | 5.0 |
| Tolnaftate | N.T. | 0.02 | N.T. |

TABLE 7

In Vitro Antifungal Activity of A89271 E
and I in Antibiotic 3 Broth (Difco)

| Compound | MIC (mcg/mL) | | |
|---|---|---|---|
| | Candida albicans | Trichophyton mentagrophytes | Aspergillus fumigatus |
| A89271 E | 5.0 | 5.0 | >80 |
| A89271 I | 1.25 | 5.0 | >80 |
| Amphotericin B | 0.02 | N.T. | 0.039 |
| Tolnaftate | N.T. | 0.02 | N.T. |

Once produced and isolated, one or more A89271 factors are useful for the inhibition of fungal growth, particularly in animals and, especially, in humans. Thus a further embodiment of this invention includes a method of inhibiting fungal growth in animals in need of such treatment comprising administering to said animal an effective amount of at least one compound selected from A89271 factor A, factor B, factor C, factor D, factor E, factor F and factor I.

Furthermore, this invention includes a method of inhibiting fungal growth in plants or plant parts comprising administering to said plant or plant part an effective amount of at least one compound selected from A89271 factor A, factor B, factor C, factor D, factor E, factor F and factor I. The term "plant" and/or "plant part" contemplates actively growing whole plants or portions thereof including, for example, leaves, flowers, stems, roots, fruit, vegetables and tubers, and also contemplates harvested and stored or processed produce from actively growing plants including, for example, fruit, grains, tubers, vegetables, leaves, fiber and seeds.

The method is carried out by applying one or more of the A89271 factors described above to plants or plant parts where the factor(s) come into contact with plant phytopathogens. Those skilled in plant protection will understand that use of the method does not necessarily kill the organisms. Depending on the application rate, the species and vigor of the phytopathogen, and the individual compound chosen, a greater or lesser proportion of the phytopathogen population will be killed and injured. It is well known that reducing the adverse effects of a phytopathogen, even though the disease is not completely eliminated, is of significant benefit to the treated plant.

It is most effective to apply the compound to a plant or plant part before the appearance of signs of infection. Thus, agriculturists can use the method for the prevention of disease by applying one or more of the factors at times when climatic factors are favorable for the growth of phytopathogens. Plants and plant parts can thereby be protected by injury which inevitably results from a pathogenic infection.

For actively growing plants, best results are obtained by applying the compound several times during a growing season at intervals of from one to a few weeks, depending upon the weather and the severity of the disease.

The methods of formulating A89271 factors and preparing dispersions of the formulations, and the methods of applying dispersions of the factors to plants and plant parts to be protected, are entirely conventional in the plant protection art.

In an especially preferred embodiment of the present invention, the A89271 factors of this invention are useful for treating susceptible neoplasms, particularly leukemia and solid tumors such as pancreatic, colonic and mammary tumors. Although A89271 factors are generally useful for the treatment of susceptible neoplasms, factors A, F and I are especially useful for treating solid tumors in mammals, particularly humans.

Thus, this invention includes a method of treating susceptible neoplasms in mammals in need of such treatment comprising administering to said mammal an effective amount of at least one compound selected from A89271 factor A, factor B, factor E, factor F and factor I.

Table 8 summarizes the activity of select A89271 factors on certain solid tumor cell lines. The method of performing the disk diffusion soft agar colony fermentation assay is described in Chapter 3 of *Cytotoxic Anticancer Drugs: Models and Concepts for Drug Discovery and Development* (Frederick A. Valeriote, et al., eds., 1990). In addition to the procedure taught in this reference, one mL ethanol was added to each dry factor in a vial, and the desired concentration of solution was placed on a paper disk. The disk was dried and then placed on soft agar plates as described in the reference.

TABLE 8

Disk Diffusion Soft Agar Colony Formation Assay[1,2]

| A89271 Factor (mcg/disk) | L1210 | P03 | C38 | Mam17 | CX-1 | H8 | LML |
|---|---|---|---|---|---|---|---|
| Factor A | 0–400[2] | 650 | 650 | | 600–650 | | |
| (45 ug) | | | 670 | | | | |
| | | | 750 | | | 300–470 | 0–300 |
| (11 ug) | 250–320 | | 610 | | | 250–420 | 0–300 |
| (9 ug) | 200–250 | 500 | 480 | | | 200–330 | |
| Factor B | 210 | | | 220 | 220 | | 0–250 |
| (80 ug) | 200–250 | | 430 | | | 200–300 | 80–250 |
| (20 ug) | 100–200 | | 260–400 | | | 180 | 0–100 |
| Factor E | 280 | | 300 | 350 | | | |
| (80 ug) | 250–300 | 440–500 | | | | 220–240 | 100–180 |

TABLE 8-continued

| Disk Diffusion Soft Agar Colony Formation Assay[1,2] | | | | | | | |
|---|---|---|---|---|---|---|---|
| A89271 Factor | | | | Solid Tumors | | | |
| (mcg/disk) | L1210 | P03 | C38 | Mam17 | CX-1 | H8 | LML |
|  | 200–220 | 460 | 480–500 |  |  |  |  |
| (20 ug) | 100–200 |  | 300–360 |  |  | 100–180 | 80 |
| Factor F | 200–250 | 500 | 500 |  |  | 200–300 |  |
| (80 ug) | 350–460 |  | 550–580 |  |  | 200–400 | 0–120 |
| (20 ug) | 300–350 |  | 590 |  |  | 200–350 | 0–80 |
| (16 ug) | 0–220 | 440 | 460 |  |  | 200–330 |  |
| (8 ug) | 250–280 |  |  | 250 |  |  | 0–400 |
| Factor I | 260 |  |  | 250 |  |  | 0–200 |
| (80 ug) | 200–220 | 490 | 500 |  |  |  | 100–200 |
| (20 ug) | 100–250 |  | 680 |  |  | 100–180 | 0–180 |
| (16 ug) | 110 | 420 | 390 |  |  | 120 |  |

[1]Key:
L1210 = murine leukemia cell line
P03 = murine pancreatic solid tumor cell line
C38 = murine colon solid tumor cell line
Mam17 = murine mammary solid tumor cell line
CX-1 = human colon solid tumor cell line
H8 = human colon solid tumor cell line
LML = "Low Malignancy Line" fibroblast
[2]Measurement in zone units; 200 zone units = 6 MM In an additional preferred embodiment, the invention is directed to a pharmaceutical composition comprising an effective amount of at least one compound selected from A89271 factor A, factor B, factor C, factor D, factor E, factor F and factor I, together with a pharmaceutically acceptable carrier, excipient or diluent, which is used for administration to an animal.

As used above and throughout this specification, the term "effective amount" means that dosage of active compound(s) sufficient to provide therapeutic treatment of the specified medical indication.

The term "active compound", as used throughout this specification, refers to at least one compound selected from A89271 factors A–F and I.

For therapeutic treatment of the specified indications, one or more A89271 factors may be administered as such, or can be compounded and formulated into pharmaceutical compositions in unit dosage form for parenteral, transdermal, rectal, nasal or intraveneous administration or, preferably, oral administration. Such pharmaceutical compositions are prepared in a manner well known in the art and comprise at least one active compound selected from the A89271 factors associated with a pharmaceutically acceptable carrier. In such a composition, the active compound is known as "active ingredient". In making the compositions, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Some examples of suitable carriers, excipients, and diluents include lactose, dextrose, sucrose, sorbitol, mannitol, starches, gum acacia, calcium phosphate alginates, calcium sailcate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient(s) after administration to the patient by employing procedures well known in the art. For oral administration, a factor, optionally including one or more additional factors, can be admixed with carriers and diluents, molded into tablets or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 1 to about 500 mg and, more frequently, from about 5 to about 300 mg of the active ingredient(s). The term "unit dosage form" refers to physically discrete units suitable as unitary dosages for human subjects and other animals, each unit containing a predetermined quantity of active material calculated to produce the desired therapeutic effect, in association with the required pharmaceutically acceptable carrier. Such compositions may contain one or more A89271 compound as an active ingredient. By "pharmaceutically acceptable", it is meant the carrier, diluent or excipient must be acceptable with the other ingredients of the formulation and not deleterious to the recipient thereof.

The following formulation examples are illustrative only and are not intended to limit the scope of the invention in any way. The meaning of the term "active ingredient" is as defined above.

Formulation 1

Hard gelatin capsules are prepared using the following ingredients:

|  | Quantity (mg/capsule) |
|---|---|
| Active ingredient(s) | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient(s) | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Active ingredient(s) | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient(s) | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl- pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient(s) | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient(s) | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient(s) | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient(s) | 100 mg |
|---|---|
| Isotonic saline | 1,000 ml |

The A89271 compounds are effective against fungal infections and susceptible neoplasms over a wide dosage range. For example, daily dosages will normally fall within the range of about 0.1 mg/kg to about 50 mg/kg of body weight. In the treatment of adult humans, the dosage range from about 5 mg/kg to about 25 mg/kg, in single or divided doses, is preferred. However, it will be understood that the amount of the compound actually administered will be determined by a physician in light of the relevant circumstances including the relative severity of a disease state, the choice of compound or compounds to be administered, the age, weight, and response of the individual patient, and the chosen route of administration. Therefore, the above dosage ranges are not intended to limit the scope of this invention in any way. Dosage ranges for second component compounds are known in the art and should be used accordingly.

In order to illustrate this invention, the following examples are provided.

General Methods.

$^1$H and $^{13}$C nuclear magnetic resonance (NMR) chemical shifts are referenced to solvent peaks: $\delta_H$ 7.26 (residual CHCl$_3$) and $\delta_c$ 77.0 for CDCl$_3$ and $\delta_H$ 3.30 (residual CHD$_2$OD) and $\delta_c$ 49.0 for methanol-d$_4$. Homonuclear $^1$H connectivities were determined with a COSY experiment, and heteronuclear $^1$H–$^{13}$C connectivities were determined by HMQC (A. Bax et al., J. Magn. Reson. 1986, 67, and HMBC (A. Bax et al., J. Am. Chem. Soc. 1986, 108, experiments. Homonuclear $^1$H nuclear Overhauser effects (NOE's) were obtained by difference NOE experiments, using a 3 s irradiation period. Optical rotations were determined in a 5-cm microcell. Table 9 provides approximate Rf values of the A89271 factors on silica gel thin-layer chromatography (TLC).

TABLE 9

TLC Rf Values of the A89271 Factors

| A89271 Factor | Rf Value | Solvent System[1] |
|---|---|---|
| A | 0.47 | A |
| B | 0.83 | A |
| C | 0.75 | A |
| D | 0.21 | A |
| E | 0.77 | A |
| F | 0.67 | A |
| I | 0.29 | B |

[1]A = toluene/EtOAc (3:1)
B = hexane/dioxane (3:2)

EXAMPLE 1

Culture of *Fischerella ambigua* (Nageli) Gomont

The *F. ambigua* strain ATCC 55210 is cultured in liquid medium (modified A$_3$ M$_7$) in 20-L glass bottles containing an inorganic medium having the following composition:

| Ingredient | Amount |
|---|---|
| NaNO$_3$ | 200 mg/L |
| NH$_4$Cl | 10 mg/L |
| K$_2$HPO$_4$.3H$_2$O | 65 mg/L |
| MgSO$_4$.7H$_2$O | 50 mg/L |
| CaCl$_2$.2H$_2$O | 13 mg/L |
| 3-(N-morpholino)-propanesulfonic acid | 627 mg/L |
| Minor elements solution[a] | 1 mL/L |
| Trace elements solution[b] | 3/25 (0.12) mL/L |

Prior to autoclaving, the pH of the complete medium is adjusted to 7 with sodium hydroxide.

| Ingredient | Amount |
|---|---|
| [a]Minor Elements Solution: | |
| FeCl$_3$.6H$_2$O | 0.54 g/L |
| Na$_2$EDTA | 3.0 g/L |
| H$_3$BO$_3$ | 0.62 g/L |
| MnCl$_2$.4H$_2$O | 1.4 g/L |
| ZnCl$_2$ | 0.10 g/L |
| CoCl$_2$.6H$_2$O | 5 mg/L |
| CuCl$_2$ 2H$_2$O | 34 mcg/L |
| [b]Trace Elements Solution: | |
| | (mg/10 L of 0.1N H$_2$SO$_4$) |
| MoO$_3$ (85%) | 176.4 |
| MH$_4$VO$_3$ | 229.6 |
| Cr$_2$K$_2$(SO$_4$)$_4$.24H$_2$O | 960.2 |
| NiSO$_4$.6H$_2$O | 447.8 |
| Co(NO$_3$)$_2$.6H$_2$O | 493.8 |
| Na$_2$WO$_4$.2H$_2$O | 179.4 |
| Al$_2$(SO$_4$)$_3$ | 317.1 |
| As$_2$O$_3$ | 66.1 |
| CdCl$_2$ | 81.5 |
| SrSO$_4$ | 104.9 |
| HgCl$_2$ | 67.7 |
| PbCl$_2$ | 67.1 |
| LiCl | 305.5 |
| Rb$_2$SO$_4$ | 78.1 |
| NaBr | 64.4 |
| KI | 65.4 |
| NaF | 110.5 |
| Na$_2$SeO$_4$ | 119.4 |
| Be(NO$_3$)$_2$.3H$_2$O | 1037.0 |

Cultures are illuminated continuously at an incident intensity of 150–200 µEinsteins m$^{-2}$ sec$^{-1}$ from banks of cool-white fluorescent tubes. Generally, cultures are vigorously aerated with 1% CO$_2$ in air and incubated at 24± 1° C. After 25–30 days, the axenic alga is harvested by filtration and freeze-dried. Yields of lyophilized alga are typically about 0.4 g/L.

EXAMPLE 2

Mass Cultivation of *Hapalosiphon hibernicus* ATCC 55225 or *Westiellopsis prolifica* UH isolate EN-3-1

The *Hapalosiphon hibernicus* ATCC 55225 and *Westiellopsis prolifica* UH isolate EN-3-1 strains are cultured as described in Example 1. Yields of lyophilized alga are typically about 0.2 to 0.3 g/L for *H. hibernicus* and about 0.1 g/L for *W. prolifica*.

EXAMPLE 3

Isolation of A89271 A–F and

Hapalindoles G and H from *Fischerella ambigua*

ATCC 55210

Lyophilized *F. Ambigua* ATCC 55210 (83 g), prepared as described in Example 1, was extracted with $CH_2Cl_2$/2-propanol. The extract (4.07 g) was chromatographed on a 1.1-m×5-cm column of Sephadex LH-20, using MeOH as the eluant. The fractions that were active against *Candida albicans* by disk assay were combined into two pools and evaporated. The residue from pool 1 (242 mg) was dissolved in 50 mL MeOH and filtered through 10 g of C18 silica. The filtrate (202 mg) was then chromatographed on a 30-cm× 2.5-cm column of C18 silica (Chromegabond MC18, ES Industries) using a linear gradient of 80–100% MeOH in water. The fungicidal fractions from this column were combined and evaporated to give A89271 B (11.3 mg) and a second residue (38 mg).

Further purification of the second residue by preparative TLC on silica gel with 3:1 toluene/EtOAc gave A89271 A (21 mg) and a mixture of A89271 C and A89271 E. The mixture was separated into pure C (4 mg) and E (7 mg) by preparative silica TLC with 3:2 hexane/dioxane.

The residue from pool 2 (338 mg) was chromatographed on $C_{18}$ silica gel in a similar manner as the pool 1 material to give A89271 D (8.5 mg) and A89271 F (25 mg), along with hapalindoles G (10.5 mg) and H (12.5 mg, $[\alpha]_D$ +217.73°).

EXAMPLE 4

Isolation of A89271 I

Lyophilized *F. ambigua* ATCC 55210 (33.55 g), prepared as described in Example 1, was extracted as described in Example 3 to yield 1.73 g of extract. This material was dissolved in 100 mL MeOH and filtered through 15 g of C18 adsorbent. The filtrate (995 mg) was chromatographed over Sephadex LH-20 as described in Example 3 to yield a pool (150 mg) containing indoles.

This material was chromatographed over a C18 preparative column as described supra, using a gradient of 80%–88% MeOH/$H_2O$ and collecting 5-mL fractions (5 mL/min flow rate). Fractions 42–50 contained A89271 factors A and E; fractions 52–58 contained hapalindole G; and fractions 59–62 contained A89271 I.

The A89271 I-containing fractions were combined and concentrated to yield a residue (7.6 mg) which was purified by preparative TLC on silica gel (hexane:dioxane, 3:2) to afford 4.5 mg of A89271 I.

EXAMPLE 5

Isolation of A89271 Factors B and F from

Hapalosiphon hibernicus

Lyophilized *H. hibernicus* ATCC 55225 (25 g), prepared as described in Example 2, was extracted in a blender three times with 1-L portions of 70% ethanol. The filtered extracts were combined and evaporated. The semisolid residue (4.72 g) was chromatographed on C18 reversed-phase silica gel (50 g), using a steep-stepped gradient from water to methanol to dichloromethane. The fractions that contained indole alkaloids by $^1H$ NMR and TLC (3:1 toluene/EtOAc) analyses were combined (1.4 g) and further partitioned by flash column chromatography on silica gel (40 g), using hexane-EtOAc mixtures. The fractions eluted with 4:1 hexane-EtOAc (138 mg) contained essentially pure A89271 B. Fraction 7 (290 mg) was further chromatographed on C18 reversed phase silica gel using a solvent gradient similar to that described supra. Fractions 32–46 contained only A89271 F by $^1H$ NMR and TLC analyses. Fraction 5 (180 mg) was recrystallised from hexane-$CH_2Cl_2$ to yield A89271 F (100 mg) as white needles.

EXAMPLE 6

Isolation of A89271 B from

*Westiellopsis prolifica*

Lyophilized *W. prolifica* EN-3-1 (17.3 g) was extracted with 70% ethanol (1 L) by blending (×3). The filtered extract was evaporated to give a semisolid residue (3.5 g). The crude extract was fractionated by flash column chromatography on C-18 reversed phase material (50 g), using a steep-stepped gradient from water to methanol to dichloromethane. Fractions 6–10 contained A89271 factors by $^1H$ NMR spectroscopy and TLC. These fractions were recombined (1.25 g) and further partitioned by flash column chromatography on silica gel (150 g), using hexane-EtOAc mixtures. Fraction 5 from this column (32 mg) contained predominantly A89271 B by $^1H$ and $^{13}C$ NMR spectroscopy. This fraction was recrystallised from hexane-$CH_2Cl_2$ to give pure A89271 B as white needles (13 mg).

EXAMPLE 7

Support for Structural Formulas of

A89271 A–F and I

1) A89271 A
  a) Characteristics $[\alpha]_D$ −30° (MeOH, c 0.1 );

CD (MeOH) λ nm [θ]: 228 (−30,200), 248 (1,000), 272 (−11,000), 303 (18,100);

UV (MeOH) $\lambda_{max}$ nm (ε): 227 (13,900), 301 (2,170);

IR (KBr) $v_{max}$: 3500, 3007, 2977, 2933, 2123, 1391, 1371, 1188, 1043, 1003, 937 $cm^{-1}$.

$^1H$ NMR (500 MHz, $CDCl_3$) δ (multiplicity, J in Hz; assignment; NOE's): 7.12 (dd, J=7.3 and 0.7 Hz; H-5; 6,17), 7.31 (m, J=7.8 and 7.3 Hz; H-6; 5, 7), 7.32 (m, J=7.8 and 0.7 Hz; H-7; 6), 4.09 (dd, J 12.3 and 3.9 Hz; H-13; 14eq, 15, 20), 2.17 (ddd, J=−12.8, 3.9 and 2.7 Hz; H-14eq; 13,14ax, 15,17), 2.47 (q, |J|=12.8 Hz; H-14ax; 14eq, 18,19), 1.64 (br ddd, J=12.8, 2.7 and 1.2 Hz; H-15; 13, 14eq, 17), 1.35 (s;

H3-17; 5,14eq, 15), 1.39 (s; H₃-18; 3-OH, 10-OH, 14ax), 1.68 (s; H3-19; 10-OH, 14ax, 21Z,26), 5.96 (dd, J=17.3 and 11.1 Hz; H-20; 13,21Z,21E), 5.37 (d, J=17.3 Hz; H-21Z; 19,20,21E, 26), 5.53 (d, J=11.1 Hz; H-21E; 20,21Z), 3.11 (d, J=4.3 Hz; H-25; 26,27), 3.55 (d, J=4.3 Hz; H-26; 19,21Z, 25), 1.73 (s; H₃-27; 25), 1.72 (s; H3-28; none), 2.91 (s; OH on C-3; 10-OH, 18), 4.26 (d, J=1.2 Hz; OH on C-10; 3-OH, 18, 19);

¹³C NMR ( 125 MHz, CDCl₃) d (multiplicity, position; ¹H-HMBC): 187.4 (s, C2; 3-OH, 25,27,28), 83.0 (s, C3; 3-OH, 10-OH), 147.1 (s, C4; 5,6,7,15,17,18), 120.0 (d, C5; 6, 7), 130.7 (d, C6; 5), 118.8 (d, C7; 5), 152.0 (s, C8; 5, 6, 7), 135.8 (s, C9; 3-OH, 5, 7), 77.7 (s, C10; 3 -OH, 10-OH, 14eq, 14ax, 26), 68.1 (s, C11; 10-OH, 19,20,25,26), 51.2 (s, C12; 13,14eq, 14ax, 19,20, 21Z, 21E, 26), 63.8 (d, C13; 14eq, 14ax, 15, 19,20), 29.0 (t, C14; 13,15), 53.3 (d, C15; 13,14eq, 14ax, 17,18,10-OH), 38.8 (s, C16; 5,15,17,18), 26.3 (q, C17; 15, 18), 25.6 (q, C18; 17), 13.9 (q, C19; 13,20), 140.5 (d, C20; 13,19,21Z), 120.3 (t, C21; none), 164.5 (s, C23; none), 39.1 (s, C24; 25,26,27,28), 64.6 (d, C25; 26,27,28), 60.3 (d, C26; none), 30.6 (q, C27; 25,28), 26.6 (q, C28; 25, 27).

FABMS m/z 453/455 (3:1 MH+ ion cluster);
HR FABMS m/z 453. 1953 (C₂₆H₃₀N₂O₃Cl, Δ–0.8 mmu).

b) Analysis of Characteristics

NMR analysis indicated the presence of 26 carbon and 29 hydrogen atoms. Twenty-six signals were observed in the ¹³C NMR spectrum for five methyl, two methylene, eight methine, and eleven quaternary carbons. In an HMQC experiment the 15 protonated-carbon signals correlated with 17 of the 19 proton signals in the ¹H NMR spectrum. The two remaining proton signals (2.91 and 4.26 ppm) were assigned to two exchangeable protons. Because FAB MS showed a 3:1 protonated molecular ion cluster at m/z 453/455, A89271 A had to have a single chlorine atom, two nitrogen atoms and three oxygen atoms to account for the multiplicity of the ion cluster and the remaining mass units. A high resolution mass measurement confirmed the molecular formula C₂₆H₂₉N₂O₃Cl which required 13 units of unsaturation.

Only ten signals were present in the 100-200 ppm region of the ¹³C NMR spectrum. Six peaks were assigned to the carbons of a trisubstituted benzenoid ring, two more to the carbons of a vinyl group, and another to an isonitrile carbon. The remaining signal (δ187.4) was consistent with an imino carbon and suggested that A89271 A was an indolenine. A89271 A could not be an indole because its UV spectrum is atypical of an indole and its NMR spectra lacks signals for an sp²-type C3 and an indole NH. Because only seven of the thirteen units of unsaturation could be accounted for by π-bonds, A89271 A had to be hexacyclic.

Two of the oxygen atoms are in hydroxyl groups (δ_H 2.91 and 4.26) attached to quaternary carbons (δ_c 83.0 and 77.7). The third oxygen appeared to be in an epoxide ring (δ_H 3.11 and 3.55; δ_c 64.6 and 60.3).

Comparison of the NMR data (including HMBC and NOESY) indicated that A89271 A had the same structure as A89271 C from C4 to C21, but differed in having a hydroxyl group on C3, C26 of the five-carbon substituent on C2 fused to C11, and an epoxide oxygen attached to C25 and C26. The hydroxyl on C10 was axial because NOE's could be seen between the OH proton and the axial methyl groups on C12 and C16. A hydroxyl group was also on C3 and syn to the OH on C10 since (1) NOEs were visible between the two OH protons and between the OH proton on C3 and the axial methyl group on C16 and (2) HMBC correlations were found between the OH proton signal and the C2, C3, C9, and C10 signals. As in A89271 B, C and E, infra, a gem-dimethyl group is attached to C2 since HMBC correlations were observed between the protons of the two methyl groups (1.72 and 1.73 ppm) and C2. The remaining atoms, i.e. those of a 1,2-disubstituted epoxide ring, had to be connected to the gem-dimethyl group and C11 since HMBC correlations were found between H26 and C10, C11, C12, C24 and C25 and between H25 and C24, C27 and C28. The fact that the protons on the epoxide ring were oriented as shown in was based on the NOEs between (1) H25 and the protons on C26 and C27 and (2) H26 and the protons on C19, C21 (E only), and C25.

c) X-Ray Crystallographic Analysis of A89271 A

A89271 A crystallized from MeOH/water in the monoclinic space group P2₁ with a unit cell having the dimensions a=7.492 (2) Å, b=12.418(3) Å, c=13.686(6) Å, β=94.55(3) Å and a calculated density of 1.27 g cm⁻³. A total of 1803 reflections with 2q less than 116.0 was measured on a Siemens R3m-V X-ray diffractometer using copper radiation. The structure was solved using direct methods and was refined by least squares with anisotropic temperature factors for all atoms except hydrogen. All hydrogen atoms were included at calculated positions. The final R-factor was 0.06 for 1668 unique observed reflections. Thus, the gross structure and relative stereochemistry of A was confirmed by X-ray crystallography.

2) A89271B a) Characteristics

Mp>3000;
[α]_D –37° (MeOH, c 0.1)
CD (MeOH) λnm [θ]: 225 (20,800), 236 (–11,000), sh 255 (–6,800), 280–292 (–1,300), 300–310 (–4,700);
UV (MeOH) λ_max nm (ε): 225 (32,400) 282 (7,600);
IR (KBr) n_max: 3620, 3487, 2975, 2142, 1602, 1467, 1445, 1231, 1046, 924 cm⁻¹.

¹H NMR (500 MHz, CDCl₃) δ (multiplicity, J in Hz; assignment; NOE's): 8.03 (br s; 1-NH; 7,27,28), 7.00 (dd, J= 7.4 and 0.7 Hz; H-5; 6,1), 7.12 (m, J=7.9 and 7.4 Hz; H-6; 5, 7), 7.13 (m, J=7.9 and 0.7 Hz; H-7; 1 -NH, 6), 3.22 (dd, J= 11.2 and 2.3 Hz; H-10; 11,14ax, 18, 19), 4.67 (d, J=2.3 Hz; H-11; 10, 19, 25, 26Z, 27, 28), 4.41 (dd, J=12.5 and 4.4 Hz; H-13; 14eq, 15), 2.44 (ddd, J=–13.0, 4.4 and 2.8 Hz; H-14eq; 13, 14ax, !5, 17), 1.94 (q, IJI=13.0 Hz; H-14ax; 10, 14eq, 18, 19), 2.22 (ddd, J=12.5, 11.2 and 2.8 Hz; H-15; 13, 14eq, 17), 1.53 (s; H3 -17; 5, 14eq, 15, 18), 1.05 (s; H3-18; 10, 14ax, 17), 1.34 (s; H3-19; 10, 11, 14ax, 20, 21Z), 6.07 (dd, J=17.6 and I1.1 Hz; H-20; 13, 19, 21Z, 21E), 5.27 (d, J=17.6 Hz; H-21Z; 19, 20), 5.34 (d, J=11.1 Hz; H-21E; 20), 6.21 (dd, J=17.6 and 10.6 Hz; H-25; 11, 26Z, 26E, 27, 28), 5.24 (dd, J=17.6 and 0.9 Hz; H-26Z; 11, 25, 27, 28), 5.21 (dd, J=10.6 and 0.9 Hz; H-26E; 25), 1.58 (s; H3-27; 1-NH ,11, 25, 26Z), 1.52 (s; H₃-28; 1-NH, 11, 25, 26Z ).

¹³C NMR (125 MHz, CDCl₃) δ (multiplicity, position; ¹H-HMBC): 137.0 (s, C2; 1-NH, 10, 25, 27, 28), 105.4 (s, C3; 1-NH, 10,11), 139.7 (s, C4; 5, 6, 7, 17, 18), 112.6 (d, C5; 6, 7), 122.2 (d, C6; none), 107.8 (d, C7; 5), 132.2 (s, C8; 1-NH, 5, 6, 7), 127.0 (s, C9; 1-NH, 5, 6, 7), 34.5 (d, C10; 11,14eq, 14ax, 15), 66.2 (d, C11; 15, 19, 20), 44.8 (s, Cl₂; 10, 11, 13, 14eq, 14ax, 19, 20, 21Z, 21E), 62.8 (d, C13; 11, 14eq, 14ax, 19, 20), 33.0 (t, C14; 10, 13, 15), 44.6 (d, C15; 10, 11, 14eq, 14ax, 17, 18), 36.5 (s, C16; 5,14eq, 14ax, 15, 17, 18), 23.9 (q, C17; 18), 24.8 (q, C18; 15,17), 16.2 (q, C19; 11, 13, 20), 142.4 (d, C20; 13, 19, 21z, 21E), 115.9 (t, C21; none), 158.6 (s, C23; 11), 38.7 (s, C24; 25, 26Z, 26E, 27, 28), 146.2 (d, C25; 26Z, 27, 28), 113.1 (t, C26; none), 27.6 (q, C27; 25, 28), 29.3 (q, C28; 25, 27).

FDMS m/z 406/408 (3:1 M+ ion cluster);

FABMS m/z 407/409 (3:1 MH+ ion cluster), 380/382 (MH+-HCN);

HR FABMS m/z 407.2207 ($C_{26}H_{32}N_2Cl$, Δ +4.7 mmu), 380.2112 ($C_{25}H_{31}NCl$, Δ +3.3 mmu).

b) Analysis of Characteristics

The field-desorption mass spectrum of B exhibited a 3:1 molecular ion cluster at m/z 406/408, and a high resolution mass measurement established the elemental composition as $C_{26}H_{31}N_2Cl$. Inspection of the $^1H$ and $^{13}C$ NMR data suggested that B was hapalindole G substituted at C2 with a 1,1-dimethyl-2-propenyl group. The signal for a proton on C2 of the indole moiety was absent, but additional signals could be seen for the presence of a second vinyl group and a second gem-dimethyl group. HMBC and NOESY experiments confirmed the proposed structure; for example, couplings were observed between C2 and the protons on N1, C10, C25, C27 and C28 in an HMBC experiment, and NOEs were evident between H11 and the protons on C26 (Z only), C27 and C28.

3) A89271 C a) Characteristics

Amorphous solid;

$[α]_D$–44° (MeOH, c 0.1)

CD (MeOH) λ nm [θ]: 224 (–7,000), 229 (–25,500), 242 (–8,700), 255 (–8,900), 291 (–5,000), 295 (–5,300);

UV (MeOH) $λ_{max}$ nm (ε) : 223 (40,700), 281 (9,400), 291 (7,700);

IR (KBr) $n_{max}$: 3486, 2976, 2144, 1442, 1227, 999, 936 cm$^{-1}$.

$^1H$ NMR (500 MHz, CDCl$_3$) δ (multiplicity, J in Hz; assignment; NOE's): 8.18 (br s; 1-NH; 7, 27, 28), 7.07 (dd, J=7.3 and 0.8 Hz; H-5; 6, 17, 18), 7.17 (m, J=8.1 and 7.3 Hz; H-6; 5, 7), 7.15 (m, J=8.1 and 0.8 Hz; H-7; 1 -NH, 6), 4.68 (s; H-11; 10-OH, 19, 20, 21Z, 25, 26Z, 26E, 27, 28), 4.41 (dd, J=12.2 and 4.1 Hz; H-13; 14eq, 15, 20, 21Z), 2.30 (ddd, J=–13.1, 4.1 and 2.3 Hz; H-14eq; 13, 14ax, 15, 17), 2.53 (q, |J|=12.7 Hz; H-14ax; 11, 14eq, 18, 19), 2.41 (ddd, J=12.7 and 2.3 Hz; H-15; 13, 14eq, 17), 1.54 (s; H$_3$-17; 5, 14eq, 15, 18), 1.23 (s; H$_3$-18; 5, 10-OH, 14ax, 17), 1.53 (s; H3 -19; 10-OH, 11, 14ax, 20, 21Z), 6.04 (dd, J=17.6 and 10.9 Hz; H-20; 11, 13, 19, 21Z, 21E), 5.26 (d, J=17.6 Hz; H-21Z; 11, 13, 19, 20, 2! E), 5.31 (d, J=10.9 Hz; H-21E; 20,21Z), 6.33 (dd, J=17.6 and 10.4 Hz; H-25; 10-OH, 11, 26Z, 26E, 27, 28), 5.36 <d, J=17.6 Hz; H-26Z; 10-OH, 11, 25, 26E, 27, 28), 5.28 (d, J=10.4 Hz; H-26E; 11, 25, 26Z), 1.64 (s; H$_3$-27; 1-NH, 11,25,26Z,28), 1.62 (s; H3-28; 1-NH, 11, 25, 26Z, 27), 1.67 (s; 10-OH; 11, 14ax, 19, 25, 26E)

$^{13}C$ NMR (125 MHz, CDCl$_3$) δ (multiplicity, position; $^1$H-HMBC): 138.8 (s, C2; 1-NH, 25, 27, 28), 111.4 (s, C3; 1-NH, 10-OH, 11), 139.8 (s, C4; 6, 17, 18), 114.4 (d, C5; 6, 7), 122.9 (d, C6; none), 107.6 (d, C7; 5), 131.8 (s, C8; 1-NH, 6), 125.4 (s, C9; 1-NH, 5, 7), 73.8 (s, C10; 11, 14eq, 14ax, 15, 10-OH), 68.5 (d, C11; 15, 19, 20, 100H), 45.3 (s, C12; 11, 13, 14eq, 14ax, 19, 20, 21Z, 21E), 63.9 (d, C13; 11, 14eq, 14ax, 15, 19, 20), 29.1 (t, C14; 13, 15), 48.0 (d, C15; 11, 13, 14eq, 14ax, 17, 18), 36.7 (s, C16; 5, 14eq, 14ax, 17, 18), 27.1 (q, C17; 15,18), 26.5 (q, C18; 15, 17), 18.5 (q, c19; 11, 13, 20), 144.2 (d, C20; 13,19,21Z), 115.5 (t, C21; none), 159.0 (s, C23; 11), 39.0 (s, C24; 25, 26Z, 26E, 27, 28), 146.8 (d, C25; 26Z, 27, 28), 112.7 (t, C26; none), 27.6 (q, C27; 25, 28), 28.9 (q, C28; 25, 27);

FDMS m/z 421/423 (3:1 [M-H]+ ion cluster);

FABMS m/z 423/425 (3:1 MH$^+$ ion cluster);

HR FABMS m/z 423.2197 ($C_{26}H_{32}N_2OCl$ Δ +0–6 mmu).

b) Analysis of Characteristics

Mass spectrometry fixed the molecular formula for A89271 C as $C_{26}H_{31}N_2OCl$. The $^1H$ NMR spectrum of A89271 C lacked a signal for H10 that B had, but possessed a signal at 1.67 for a hydroxyl proton. The hydroxyl group appeared to be on C10 since the OH proton signal showed two and three-bond HMBC correlations to C3, C10, C11, C15. The hydroxyl group on C10 had to be axial because the signals for the axial proton on C14 and the protons of the axial methyl groups on C12 and C16 were shifted downfield significantly and NOEs were observed between the OH proton and the protons on C11, C14 (axial only), C19, C25 and C26 (E only). A89271 C, therefore, has a structure like that of hapalindole V except that A89271 C has a 1,1-dimethyl-2propenyl group at the C2 position.

4) A89271 D a) Characteristics

Amorphous solid;

$[α]_D$–18° (MeOH, c 0.1);

CD (MeOH) λ nm [q]: 221 (31,300), 231 (–18,000), 268 (1,500), 300 (–2,500);

UV (MeOH) $λ_{max}$ nm (ε): 224 (36,000), 280 (7,200), 290 (5 500);

IR (KBr) $n_{max}$: 3020, 2131, 1701, 1445, 1250, 1033 cm–1.

$^1H$ NMR (500 MHz, CDCl$_3$) δ (multiplicity, J in Hz; assignment; NOE's): 8.08 (br s; 1-NH; 7, 27, 28), 7.08 (dd, J= 7.2 and 0.7 Hz; H-5; 6, 17, 18), 7.15 (dd, J=7.7 and 0.7 Hz; H-7; 1-NH, 6), 7.21 (dd, J=7.7 and 7.2 Hz; 1-NH, 6.53 (dd, J=12.7 and 3.6 Hz; H-13; 14eq, 15, 20), 2.32 (ddd, J= –12.7, 3.6 and 2.7 Hz; H14eq; 13, 14ax, 15, 17), 2.61 (q, |J| =12.7 Hz; H-14ax; 14eq, 18, 19), 2.46 (br dd, J=12.7 and 2.7 Hz; H-15; 13, 14eq, 17), 1.53 (s; H3-17; 5, 14eq, 15,18) 1.37 (s; H3-18; 5, 10-OH, 14ax, 17), 1.84 (s; H3-19; 10-OH, 14ax, 21Z, 26, 26-OH), 6.08 (dd, J=17.2 and 11.1 Hz; H-20; 13, 21Z, 21E, 26), 5.43 (d, J=17.2 Hz; H-21Z; 19, 20, 21E, 26), 5.54 (d, J=11.1 Hz; H-21E; 20,21Z), 4.65 (dd, J=5.0 and 1.8 Hz; H-26; 19, 21Z, 25, 26-OH), 4.22 (br s; H-25; 26,27), 1.60 (s; H3-27; i-NH, 25), 1.43 (s; H3-28; 1-NH, 10-OH, 26-OH), 3.61 (s; OH on C-10; 18, 19, 26-OH, 28), 2.55 (br s; OH on C25; 10-OH, 26-OH), 4.01 (d, J=5.0 Hz; OH on C-26; 10-OH, 19, 26, 28).

$^{13}C$ NMR (125 MHz, CDCl$_3$) δ (multiplicity, position; $^1$H-HMBC): 136.9 (s, C2; 1-NH, 27, 28), 110.4 (s, C3; 1-NH), 139.3 (s, C4; 6,17,18), 114.7 (d, C5; 7), 123.1 (d, C6; none), 107.3 (d, C7; 5), 133.0 (s, C8; 1-NH, 6), 124.7 (s, C9; 1-NH, 5, 7), 77.8 (s, C10; 10-OH, 14eq, 14ax, 15, 26), 70.3 (s, C11; 10-OH, 19, 20, 26, 26-OH), 50.7 (s, C12; 13, 14eq, 14ax, 19, 20, 21Z, 21E, 26), 65.4 (d, C13; 14eq, 14ax, 15, 19, 20), 29.0 (t, C14; 13, 15), 49.4 (d, C15; 10-OH, 13, 14eq, 14ax, 17, 18), 37.6 (s, C16; 5, 15, 17, 18), 28.8 (q, C17; 18), 26.6 (q, C18; 15, 17), 13.2 (q, C19; 13,20), 141.3 (d, C20; 13, 19, 21Z), 120.2 (t, C21; none), 163.0 (s, C23; none), 40.4 (s, C24; 26, 27, 28), 73.9 (d, C25; 26, 27, 28), 80.7 (d, C26; 26-OH), 28.1 (q, C27; 28), 27.0 (q, C28; 25, 27).

FDMS m/z 454/455/456/457 (overlapping 3: 1 M+ and MH$^+$ ion clusters );

HR MS m/z 454.2009 ($C_{26}H_{31}N_2O_3Cl$, D +1.4 mmu).

b) Analysis of Characteristics

FAB MS showed a 3:1 MH$^+$ ion cluster at m/z 454/456, and HR MS established the molecular formula as $C_{26}H_{31}N_2O_3Cl$. The UV spectrum and a NH signal at 8.08 ppm in the $^1H$ NMR spectrum were consistent with an indole. The NMR data showed that A89271 D is similar in structure to A89271 F, infra, the difference being that the epoxide ring is replaced by a trans diol unit. The $^1H$ NMR spectrum gave signals at 4.22 (H25) and 4.65 (H26) ppm which were coupled to each other and to hydroxyl proton signals at 2.55 and 4.01 ppm, respectively. An HMBC experiment showed that the trans diol unit was connected to C11 and C24, since cross peaks were present between the H26 signal and the signals for C10, C11, C12, C24 and C25. A NOESY experiment established that the OH group on C26 was syn to the methyl group on C12 and the OH group on C10, since NOE'S could be seen between (1) the 26-OH proton and the protons of 10-OH, the axial methyl group on C12, and the pro-R methyl group on C24 and (2) H26 and the Z proton on C21.

5) A89271 E a) Characteristics

Amorphous solid;

$[\alpha]_D$ –9.5° (MeOH, c 0.1).

CD (MeOH) λ nm [θ]: 223 (12,600), 230 (–21,200), 241 (–4,100), 251 (–6,700), sh 270 (–3,400), sh 282 (–2,400), 291 (–2,100), 295–305 (–3,600);

UV (MeOH) $\lambda_{max}$ nm (ε) : 223 (36,000) 281 (8,400), 291 (6,800);

IR (KBr) $n_{max}$: 3486, 2970, 2146, 1700, 1603, 1441, 999, 935 cm$^{-1}$.

$^1$H NMR (500 MHz, CDCl$_3$) δ (multiplicity, J in Hz; assignment; NOE's): 8.15 (br s; 1-NH; 7, 27, 28), 7.06 (dd, J= 7.4 and 0.6 Hz; H-5; 6,17,18), 7.15 (dd, J=8.1 and 7.4 Hz; H-6; 5,7), 7.13 (dd, J=8.1 and 0.6 Hz; H-7; 1-NH, 6), 4.49 (s; H-11; 10-OH, 19, 20, 25, 26Z, 26E, 27, 28), 1.93 (ddd, J=–13.1, 12.7 and 3.6 Hz; H-13; 13eq, 14eq), 1.64 (ddd, J=–13.1, 3.6 and 3.2 Hz; H-13; 13ax, 14eq), 1.88 (dtd, J=–12.7, 3.6 and 2.3 Hz; H-14eq; 13ax, 13eq, 14ax, 15, 17), 2.11 (qd, |J|=13.0 and 3.2 Hz; H-14ax; 14eq, 18, 19) 2.21 (dd, J=12.7 and 2.3 Hz; H-15; 14eq, 17), 1.51 (s; H$_3$-17; 5, 14eq, 15, 18), 1.21 (s; H$_3$-18; 5, 14ax, 17), 1.42 (s; H$_3$-19; 11, 14ax, 20; 21Z), 5.94 (dd, J=17.6 and 10.9 Hz; H-20; 11, 19, 21Z, 21E), 5.06 (d, J=17.6 Hz; H-21Z; 19, 20, 21E), 5.08 (d, J=10.9 Hz; H-21E; 20, 21Z), 6.36 (dd, J= 17.6 and 10.4 Hz; H-25; 11, 26Z, 26E, 27, 28), 5.37 (dd, J= 17.6 and <1 Hz; H-26Z; 11, 25, 26E, 27, 28), 5.28 (dd, J= 10.4 and <1 HZ; H-26E; 11, 25, 26Z), 1.67 (s; H3 -27; 1-NH, 11, 25, 26Z, 28), 1.63 s; H3-28; 1-NH, 11, 25,26Z, 27), 1.62 (s; 10-OH; 11).

$^{13}$C NMR (125 MHz, CDCl$_3$) δ (multiplicity, position; $^1$H-HMBC): 138.5 (s, C2; 1-NH, 25, 27, 28), 112.6 (s, C3; 1-NH, 10-OH, 11), 140.6 (s, C4; 5, 6, 15, 17, 18), 114.2 (d, C5; 7), 122.6 (d, C6; 5), 107.3 (d, C7; 5), 131.7 (s, C8; 1-NH, 5, 6), 125.7 (s, C9; 1-NH, 5, 7), 74.2 (s, C10; 10-OH, 11, 14eq, 14ax, 15), 67.2 (d, C11; 10-OH, 15, 19, 20), 40.6 (s, Cl$_2$; 11, 13eq, 14eq, 14ax, 19, 20, 21Z, 21E), 31.6 (t, C13; 11, 14eq, 14ax, 15, 19, 20), 17.7 (t, C14; 13ax, 15), 47.0 (d, C15; 10-OH, 11, 13ax, 14eq, 14ax, 17, 18), 36.5 (s, C16; 5, 14eq, 15, 17, 18), 27.0 (q, C17; 15, 18), 26.6 (q, C18; 15,17), 24.1 (q, C19; 11, 13ax, 20), 147.5 (d, C20; 11, 13ax, 19, 21Z), 111.9 (t, C21; none), 157.0 (s, C23; 11), 39.0 (s, C24; 25, 26Z, 26E, 27, 28), 147.1 (d, C25; 26Z, 27, 28), 112.6 (s, C26; none), 27.8 (q, C27; 25, 28), 28.9 (q,C28, 25, 27).

FDMS m/z 388 (M$^+$);

FABMS m/z 389 (MH$^+$);

HR FABMS m/z 389.2590 (C$_{26}$H$_{33}$N$_2$O, Δ+0.3 mmU).

b) Analysis of Characteristics

The elemental composition Of A89271 E was found to be C$_{26}$H$_{32}$N$_2$O by MS. NMR analysis showed that E was the deschloro derivative of A89271 C. COSY data and coupling constants indicated that C13 to C15 was a CH$_2$—CH$_2$—CH$_{ax}$ unit. HMBC and NOESY experiments established that the OH on C10 was axially oriented.

6) A89271 F a) Characteristics

Mp>300° C. (dec);

$[\alpha]_D$ –60° (MeOH,c 0.1).

CD (MeOH) λnm [θ]: 220 (23,200), 231 (–13,400);

UV (MeOH), $\lambda_{max}$: nm (ε): 223 (36,000), 272 (7,100), 279 (6,800);

IR (KBr) $\gamma_{max}$: 3691, 3618, 2976, 2130, 1604, 1448, 1046, 944, 876 cm$^{-1}$ $^1$H NMR (500 MHz, CDCl$_3$) δ (multiplicity, J in Hz; assignment; NOE's): 7.99 (br s; 1-NH; 7,27,28), 7.06 (dd, J= 7.2 and 0.7 Hz; H-5; 6,17,18), 7.19 (dd, J=8.1 and 7.2 Hz; H-6; 5, 7), 7.09 (dd, J=8.1 and 0.7 Hz; H-7; 1-NH, 6), 4.45 (dd, J=12.7 and 3.6 Hz; H-13; 14eq, 15, 20), 2.33 (ddd, J=–12.7, 3.6 and 2.7 Hz; H14eq; 13, 4ax, 15, 17), 2.62 (q, |J|=12.7 Hz; H-14ax; 14eq, 18, 19), 2.34 (dd, J= 12.7 and 2.7 Hz; H-15; 13, 14eq, 17), 1.51 (s; H3-17; 5, 14eq, 15,18), 1.40 (s; H$_3$-18; 5, 10-OH, 14ax, 17), 1.74 (s; H$_3$-19; 10-OH, 14ax, 20, 21Z, 26), 6.16 (dd, J=17.6 and 10.9 Hz; H-20; 13, 19, 21Z, 21E, 26), 5.44 (d, J=17.6 Hz; H-21Z; 19, 20, 21Z, 26), 5.59 (d, J=10.9 Hz; H-21E; 21Z), 3.13 (d, J=4.5 Hz; H25; 26, 27, 28), 3.77 (d, J=4.5 Hz; H-26; 19, 21Z, 25), 1.62 (s; H$_3$-27; 1-NH, 25, 28), 1.67 (s; H$_3$ 28; 1-NH, 25, 27), 3.69 ( s; OH on C-10; 18, 19).

$^{13}$C NMR ( 125 MHz, CDCl$_3$) δ (multiplicity, position; 1H-HMBC): 133.5 (s, C2; 1-NH, 25, 27, 28), 109.6 (s, C3; 1NH), 139.7 (s, C4; 6, 17, 18), 114.5 (d, C5; 7), 123.2 (d, C6; 5, 7), 107.0 (d, C7; 5), 133.6 (s, C8; 1 -NH, 6), 124.1 (s, C9; 1-NH, 5,7), 75.0 (s, C10, 10-OH, 14eq, 14ax, 15, 26), 68.6 (s, C11; 19, 20, 25, 26), 50.4 (s, C12; 13, 14eq, 14ax, 19, 20, 21Z, 21E, 26), 64.4 (d, C13; 14eq, 14ax, 15, 19, 20), 28.9 (t, C14; 13, 15), 48.4 (d, C15; 10-OH, 13, 14eq, 14ax, 17, 18), 37.8 (s, C16; 5, 14eq, 14ax, 15, 17, 18), 28.4 (q, C17; 15, 18), 26.5 (q, C18; 15,17), 13.1 (q, C19; 13, 20), 141.3 (d, C20; 13,19,21Z), 120.0 (t, C21; none), 161.5 (s, C23; none), 36.1 (s, C24; 25, 26, 27, 28), 65.9 (d, C25; 26, 27, 28), 61.4 (d, C26; 25), 27.3 (q, C27; 25, 28), 29.8 (q, C28; 25, 27).

FDMS m/z 436/438 (3:1 M$^+$ ion cluster);

FABMS m/z 437/439 (3:1 MH$^+$ ion cluster);

HR FABMS m/z 437.1990 (C$_{26}$H$_{30}$N$_2$O$_2$Cl, Δ +0.7 mmu)

b) Analysis of Characteristics

HR MS revealed an elemental composition of C$_{26}$H$_{29}$N$_2$O$_2$Cl for A89271 F. Thus, it has one less oxygen than A89271 A. Analysis of the $^1$H and $^{13}$C NMR spectra, in particular those from HMBC and NOESY experiments, indicated that the structure of F was similar to the one for A. In the $^1$H NMR spectrum of F, however, the 3-OH proton signal was missing, but an indole NH signal was present at 7.99 ppm. The indole system was also established by the UV spectrum.

7) A89271 I a) Characteristics

UV (MeOH) λmax nm (ε): 223 (36,700), 272 (7,600), 279 (7,300);

$^1$H NMR (300 MHz, d6-acetone): δ 10.05 (br s, 1NH), 7.04, 6.98, 6.96 (3 d, H-5, H-6, H-7), 2.4, 2.3, 1.9, 1.86 (5 m, H-13ax, H-13eq, H-14ax, H-14eq, H-15), 1.45 (s, CH$_3$-17), 1.33 (s, CH$_3$-18), 1.73 (s, CH$_3$-19), 6.22 (dd, H-20), 5.35 (d, H-21Z), 5.31 (d, H-21E), 3.3 (d, H-25), 3.71 (d, H26), 1.67 (2s, CH$_3$-27, 28).

FABMS m/z 403 (MH+);

HR FABMS m/z 403.2394 (C$_{26}$H$_{31}$N$_2$O$_2$, Δ +0.8 mmu).

Absolute Stereochemistry. The absolute stereochemistries of A–F and I were not rigorously determined. The CD spectra of the seven compounds were determined. The spectra of B–F showed a negative peak at 230–235 nm and a positive peak at 220–225 nm, suggesting that the absolute stereochemistries of B–F are identical. The A89271 factors probably have the same absolute stereochemistry as the hapalindoles. The hapalindole G produced by the F. ambigua culture had an optical rotation identical with that of an authentic sample of hapalindole G produced by *Hapalosiphon fontinalis*, the absolute stereochemistry of which is known. Thus, the absolute configurations of A–F and I are believed to be as depicted.

We claim:

1. A compound selected from A89271 factors A, B, C, D, E, F and I as follows:

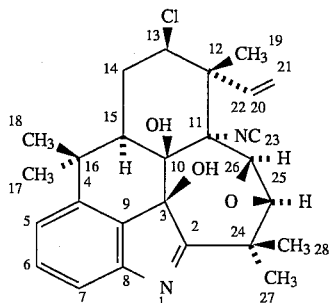

(1) A89271 A

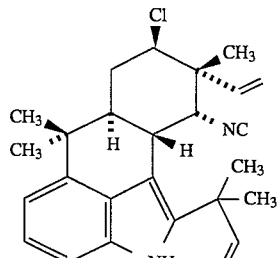

(2) A89271 B;

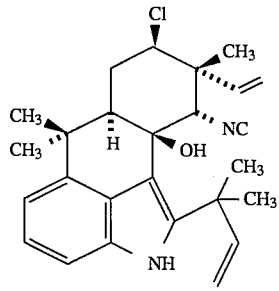

(3) A89271 C;

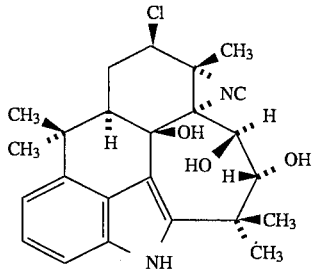

(4) A89271 D

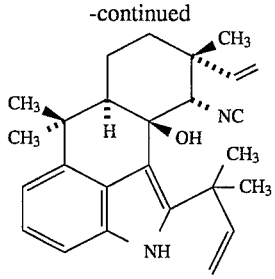

(5) A89271 E;

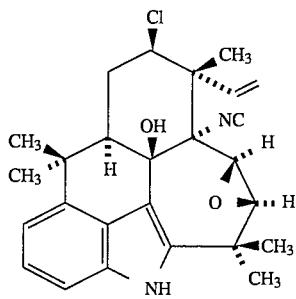

(6) A89271 F and

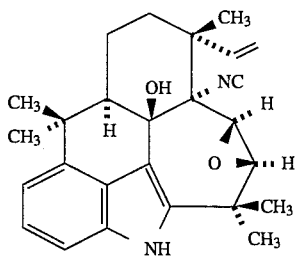

(7) A89271 I.

2. The compound of claim 1 which is A89271 A.
3. The compound of claim 1 which is A89271 B.
4. The compound of claim 1 which is A89271 C.
5. The compound of claim 1 which is A89271 D.
6. The compound of claim 1 which is A89271 E.
7. The compound of claim 1 which is A89271 F.
8. The compound of claim 1 which is A89271 I.
9. A method of inhibiting fungal growth in animals in need of such treatment comprising administering to said animals an effective amount of at least one compound selected from A89271 factor A, factor B, factor C, factor D, factor E, factor F and factor I.
10. A method of claim 9 wherein said compound is factor D.
11. A method of claim 9 wherein said compound is factor I.
12. A method of claim 11 wherein said animal is a human.
13. A method of inhibiting fungal growth in plants or plant parts comprising administering to said plant or plant part an effective amount of at least one compound selected from A89271 factor A, factor B, factor C, factor D, factor E, factor F and factor I.

14. A pharmaceutical composition comprising an effective amount of at least one compound selected from A89271 factor A, factor B, factor C, factor D, factor E, factor F and factor I, together with a pharmaceutically acceptable carrier, excipient or diluent.

* * * * *

UNITED STATES PATENT AND TRADEMARK OFFICE
CERTIFICATE OF CORRECTION

PATENT NO. : 5,457,119

DATED : October 10, 1995

INVENTOR(S) : Rosanne Bonjouklian, et al.

Page 1 of 2

It is certified that error appears in the above-indentified patent and that said Letters Patent is hereby corrected as shown below:

In Column 1, line 50, delete the term "R.E. Moore et al.," and insert therefor -- (R.E. Moore et al., --.

In column 4, line 12, delete the term "5 to micrometers", and insert therefor -- "5 to 6 micrometers --.

In column 4, line 56, delete the term "A8927!" and insert therefor -- A89271 --.

In column 13, line 39, delete the term "67, and" and insert therefor -- 67, 565) and --.

In column 13, line 40, delete the term "1986, 108," and insert therefor -- 1986, 108, 2093) --.

In column 17, line 8, delete the term "i8", and insert therefor -- 18 --.

In column 18, line 10, delete the term "in was" and inert therefor -- in $\underline{1}$ was In column 18, line 30, delete the term "Mp>3000;" and insert therefor -- Mp>300° --.

In column 18, line 44, delete the term "14ax, !5, 17)" and insert therefor -- 14ax, 15, 17) --.

In column 18, line 48, delete the term "and I1.1 Hz" and insert therefor -- and 11.1 Hz --.

In column 18, line 59, delete the term "(s, Cl$_2$;" and insert therefor -- (s, Cl2; --.

In column 19, line 43, delete the term "19, 20, 2! E)" and insert therefor -- 19, 20, 21 E --.

In column 19, line 45, delete the term "5.36 <d," and insert therefor -- 5.36 (d, --.

UNITED STATES PATENT AND TRADEMARK OFFICE
CERTIFICATE OF CORRECTION

PATENT NO. : 5,457,119

DATED : October 10, 1995

INVENTOR(S) : Rosanne Bonjouklian, et al.

It is certified that error appears in the above-indentified patent and that said Letters Patent is hereby corrected as shown below:

In column 19, line 54, delete the term "20, 100H)" and insert therefor -- 20, 10OH)--.

In column 19, line 58, delete the term "(q, c19;" and insert therefor --q, C19; --.

In column 20, line 21, delete the term "(5 500)" and insert therefor -- (5,500) --.

In column 20, line 37, delete the term "H3-27; i-NH, 25)" and insert therefor -- H3-27; 1-NH, 25) --.

In column 21, line 38, delete the term "1.63 s; H3-28" and insert therefor -- 1.63 (s; H3-28 --.

In column 21, line 58, delete the term "composition Of" and insert therefor -- composition of --.

Signed and Sealed this

Twenty-fifth Day of June, 1996

BRUCE LEHMAN

Attest:

Attesting Officer

Commissioner of Patents and Trademarks